United States Patent
Kuhr et al.

(12) 
(10) Patent No.: US 6,602,268 B2
(45) Date of Patent: Aug. 5, 2003

(54) BLOOD LANCET SYSTEM FOR BLOOD WITHDRAWAL FOR DIAGNOSTIC PURPOSES

(75) Inventors: Hans-Jurgen Kuhr, Mannheim (DE); Richard Forster, Pfreimd (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/884,305

(22) Filed: Jun. 19, 2001

(65) Prior Publication Data
US 2002/0040230 A1 Apr. 4, 2002

(30) Foreign Application Priority Data
Jun. 21, 2000 (DE) .......................... 100 30 410

(51) Int. Cl.[7] ............................... A61B 17/32
(52) U.S. Cl. ................................ 606/181
(58) Field of Search .............. 606/181, 182, 606/183–185, 167, 188

(56) References Cited

U.S. PATENT DOCUMENTS

| 4,442,836 A | 4/1984 | Meinecke et al. |
| 4,990,154 A | 2/1991 | Brown et al. |
| 5,304,193 A | 4/1994 | Zhadanov |
| 5,318,584 A | 6/1994 | Lange et al. |
| 5,324,303 A | 6/1994 | Strong et al. |
| 5,554,166 A | 9/1996 | Lange et al. |
| 5,628,765 A | 5/1997 | Morita |

FOREIGN PATENT DOCUMENTS

| DE | 19830604 A1 | 2/2000 | ............ A61B/5/15 |
| DE | 19909602 A1 | 9/2000 | ............ A61B/5/15 |
| EP | 0414563 A1 | 2/1991 | |
| EP | 0414563 B1 | 2/1991 | ............ A61B/5/14 |
| EP | 0595148 A1 | 5/1994 | ............ A61B/5/14 |
| EP | 0958783 A1 | 11/1999 | ............ A61B/5/14 |

*Primary Examiner*—Tajash Patel
(74) *Attorney, Agent, or Firm*—Jill L. Woodburn; Richard T. Knauer

(57) ABSTRACT

Blood lancet system for blood withdrawal for diagnostic purposes with a housing, a lancet holder movable in the housing for holding an exchangeable lancet, and a lancet drive for driving the pricking movement of the lancet holder with the lancet contained herein. The housing has a cap at the front end in pricking direction which can be removed in order to remove a used lancet from the lancet holder.

Figure 1:
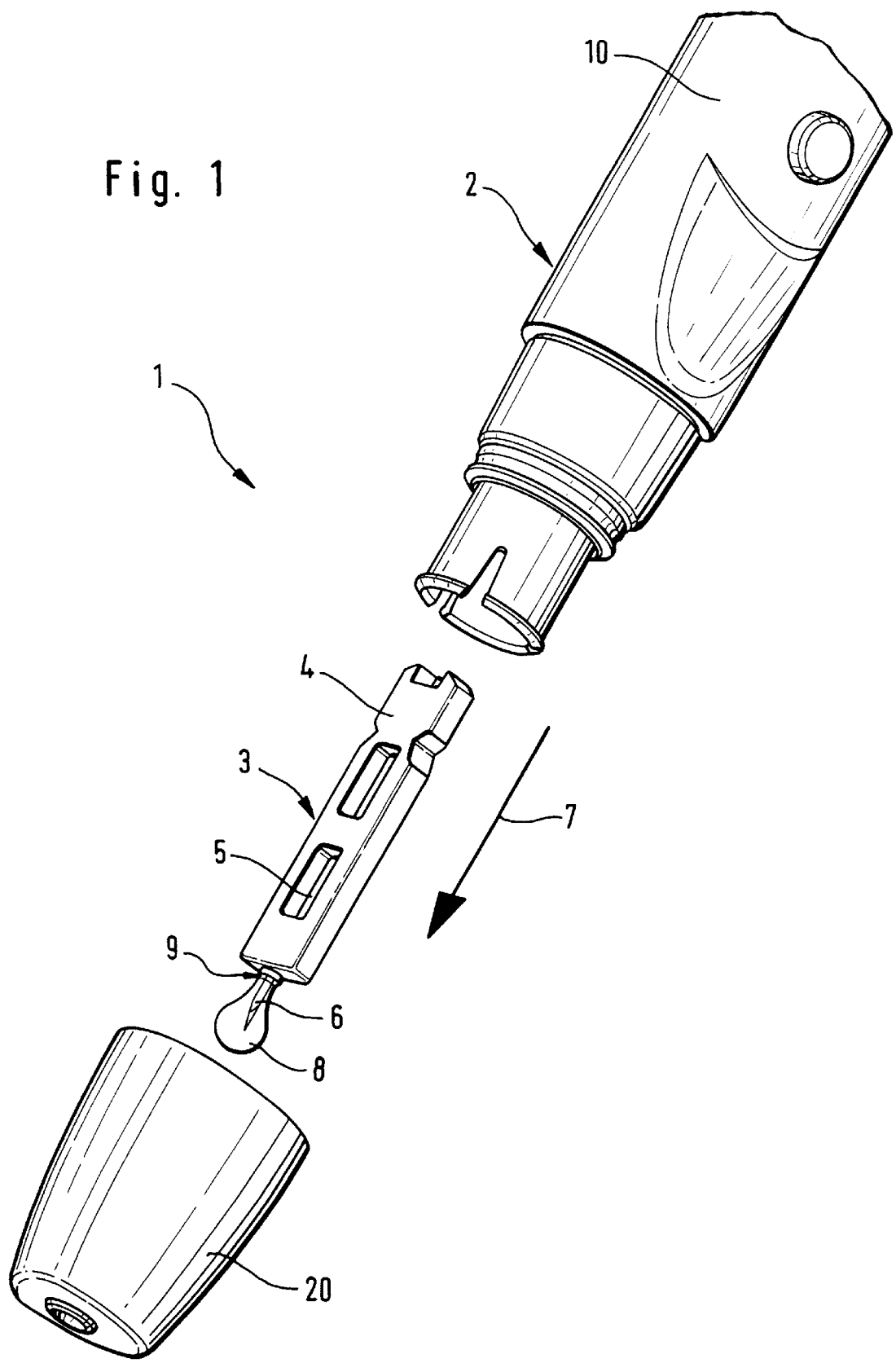

The lancet and the housing cap are coupled, during the attachment of the housing cap, by a coupling mechanism comprising coupling elements matched to each other and enabling the extraction of the lancet from the lancet holder simultaneously with removing the housing cap.

20 Claims, 5 Drawing Sheets

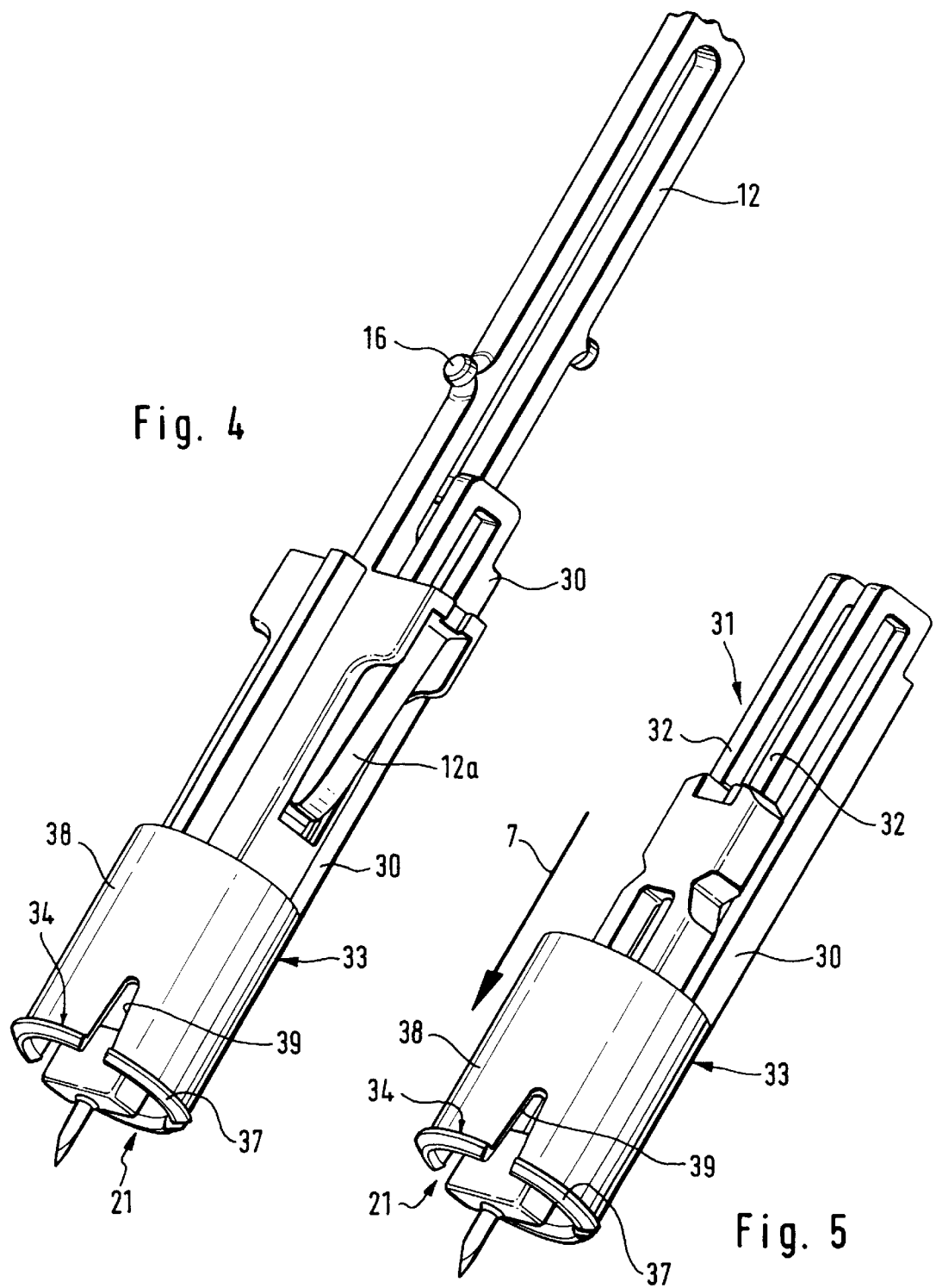

BLOOD LANCET SYSTEM FOR BLOOD WITHDRAWAL FOR DIAGNOSTIC PURPOSES

This invention is concerned with a blood lancet system for blood withdrawal for diagnostic purposes.

In case of various illnesses it is necessary to investigate the human blood with respect to a component (analyte) contained therein. To this end it is oftentimes sufficient to withdraw a small amount of blood from the body by generating a small prick wound. A particularly important such case is diabetes mellitus, which requires the blood to be investigated in regular intervals for its glucose content.

For generating the necessary prick wound, commonly blood lancet systems are used which comprise a pricking apparatus and replaceable lancets, adapted to this apparatus. The housing of the pricking apparatus contains a lancet adapted for holding the lancet in a replacable manner. During the pricking process, the lancet is driven by a lancet drive, also integrated in the lancet apparatus, in a way that the lancet is moved quickly in the pricking direction, until the lancet tip protrudes from an opening at the front end of the pricking apparatus, thus generating a small prick wound in the body part pressed against the front end. Thereafter the lancet is moved back (against the pricking direction).

When common pricking apparatuses are in their use state, the lancet holder is covered by a housing cap which forms the front end of the pricking apparatus housing and has a small opening through which the lancet tip can protrude during the pricking process. The pricking opening is surrounded by a contact surface which serves for contacting the blood lancet apparatus to the body part from which the blood shall be withdrawn during use of the blood lancet apparatus (usually the finger tip or the ear lobe).

For avoiding infections, the lancets are disposable elements designed for a single use. In order to insert a new lancet, the housing cap covering the lancet holder is removed, and the lancet is inserted into the lancet holder. The housing cap is also removed for removing used lancets.

Blood lancet systems are not only used by medical staff, but also, and to a large extent, by non-experts. This is particularly true for the therapy control of diabetics. It was determined that serious damages occurring in conjunction with diabetes (e.g. blindness) can be dramatically reduced if the glucose concentration of the diabetic's blood is measured very often (four to five times a day), adjusting the insulin injections very exactly, using these measurements. The willingness and the ability of diabetics to check their blood that often in the scope of home-monitoring highly depends on the optimal function of the blood lancet system used.

An important part of this function are the handling steps necessary for the insertion of new and the removal of used lancets. On one hand, they should be as simple as possible, and on the other hand there should be maximum safety against injury and infection risks. At the same time, the cost, in particular with respect to the disposable material, should be as low as possible.

During the insertion of the lancet, the sharp tip of the lancet needle is usually covered by a tip cover element made of plastic and allowing a secure handling of the lancet. Once the lancet is inserted, the tip cover element must be removed and the housing cap must be attached. After the pricking process, the housing cap must be removed, so that the lancet becomes accessible again. Then, the lancet can be manually removed. The risk of injury at the lancet tip, however, is very high, in particular taking into account that a large share of the users is handicapped by high age, bad vision or trembling hands.

In order to simplify the removal of the used lancet, many apparatuses are equipped with a manually operated ejection mechanism. For example, U.S. Pat. No. 5,318,584 describes a blood lancet system in which the blood lancet can be ejected from the lancet holder by means of an ejection rod; the ejection rod is actuated by pressing an actuation button provided at the rear end of the pricking apparatus. U.S. Pat. No. 4,442,836 describes an apparatus having an ejection mechanism designed in a way that the used lancet is automatically thrown out when re-cocking the apparatus after each pricking process. However, such ejection mechanisms require a relatively complicated and expensive construction. The handling is not as easy as desirable, taking into account the health state of many users.

EP 0 958 783 A1 describes a blood lancet apparatus which is equipped with so-called engagement means at the cap, which can be moved by the user from a first position, not in engagement with the lancets, into a second position, where they contact the lancet pressing it against the opposite interior wall of the cap. For actuation of the engagement means, a button may be provided which protrudes laterally from the cap. After the pricking process the user must first press this button, thus clamping the lancet in the cap, then take off the lancet together with the cap, and finally dispose the lancet. This requires an additional, difficult handling step, causing a severe problem for many users.

With the aim to achieve optimal simplicity and operational safety some known blood lancet systems have the lancet integrated into the cap, so that the lancet and the housing cap together form a replaceable, disposable unit. Such designs are described in EP-0595148 A1 and in U.S. Pat. Nos. 4,990,154 and 5,628,765. A disadvantage of this design is the high material consumption, because the entire disposable design unit, including the housing cap, has to be disposed after each use. Due to the high cost these systems are only appropriate for application areas with high safety and hygienic requirements, in particular for the use in hospitals. In the home-monitoring area, on one hand safety risks are lower since the blood lancet systems are always used by the same patient, on the other hand the cost for the integrated lancet-cap-disposables is not acceptable.

On this basis, the invention addresses the problem to provide a blood lancet system, in particular for home-monitoring, which allows a riskless and simple removal of used lancets from the lancet holder without a need to touch the lancet and with as little expense as possible.

This problem is solved by a blood lancet system for blood withdrawal for diagnostic purposes, comprising lancets and a pricking apparatus with a housing, a lancet holder movable in the housing for holding an exchangeable lancet, and a lancet drive for driving a pricking movement of the lancet on a predetermined pricking path, wherein the housing comprises a cap to be attached at a forward end thereof in pricking direction, the cap being removable for removing a used lancet out of the housing, and the lancet and the cap are coupled to each other, while the cap is attached to the housing, by a coupling mechanism comprising coupling elements matched to each other, thereby enabling the extraction of the lancet from the lancet holder simultaneously with removing the cap.

In contrast to the mentioned lancet-cap-disposables, the lancet used with the instant invention is a separate element, produced and distributed independently from the housing cap. It is the only disposable part. The cap can be used permanently, thus it can be produced with higher quality. The use is very simple as the pulling-off of the housing cap and the removal of the used lancet is performed in a single handling step.

In contrast to the design described in EP 0958783, the invention does not require any additional handling steps, as the coupling of the cap with the lancet is performed automatically during the procedure of the handling steps which are anyway necessary and common.

In the most simple case, the coupling mechanism acts directly between the housing cap and the lancet. Generally, lancets have a lancet body made of plastic, surrounding the metal lancet needle. The first of the matched coupling elements can be provided at this lancet body. The second coupling element is provided, preferably, directly at the cap (at its inner wall). For example, the lancet body may have a groove-type recess running in the direction of its longitudinal axis, in which a catch may latch in, which latch protrudes from an elastic tongue fixed at the inside wall of the cap. When the cap is attached, the protruding catch latches into the groove. The dimensions of the groove are designed in such a way that the lancet movement in pricking direction, required for the pricking process, is possible.

An embodiment in which the coupling mechanism includes an additional part designated as ejector, is preferred. The ejector is arranged in the housing in a way that it is movable in the pricking direction. It is provided with a lancet contact element which contacts the lancet during the ejection process, thus pressing or pulling it out of the holder. For this design type, a first of the matched coupling elements is arranged at the ejector, and, preferably, a second of the matched coupling elements is arranged at the cap.

The invention is explained in more detail with reference to an embodiment represented in the figures. The features described there can be applied single or in combination in order to create preferred embodiments of the invention.

Figure 2:
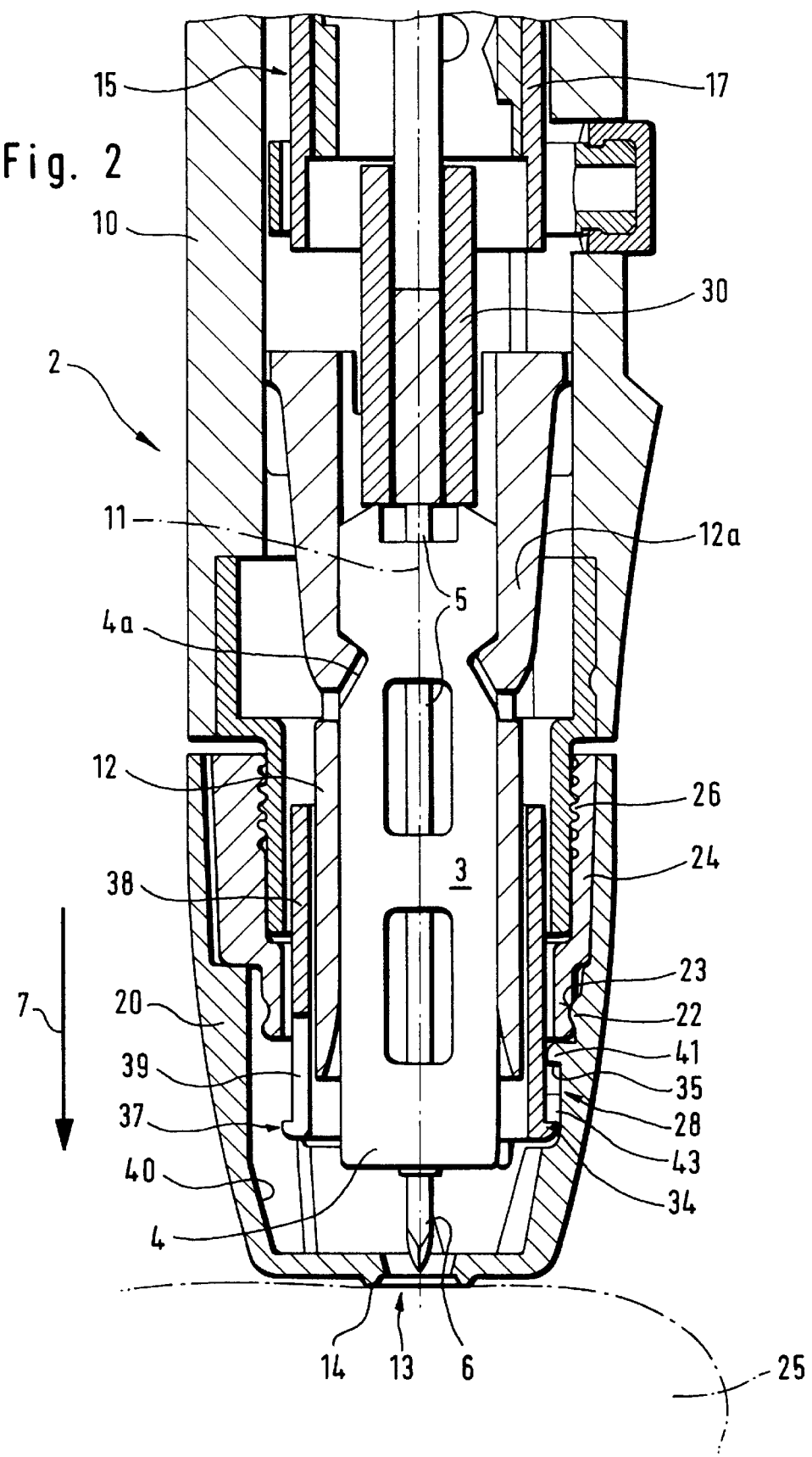
Figure 3:
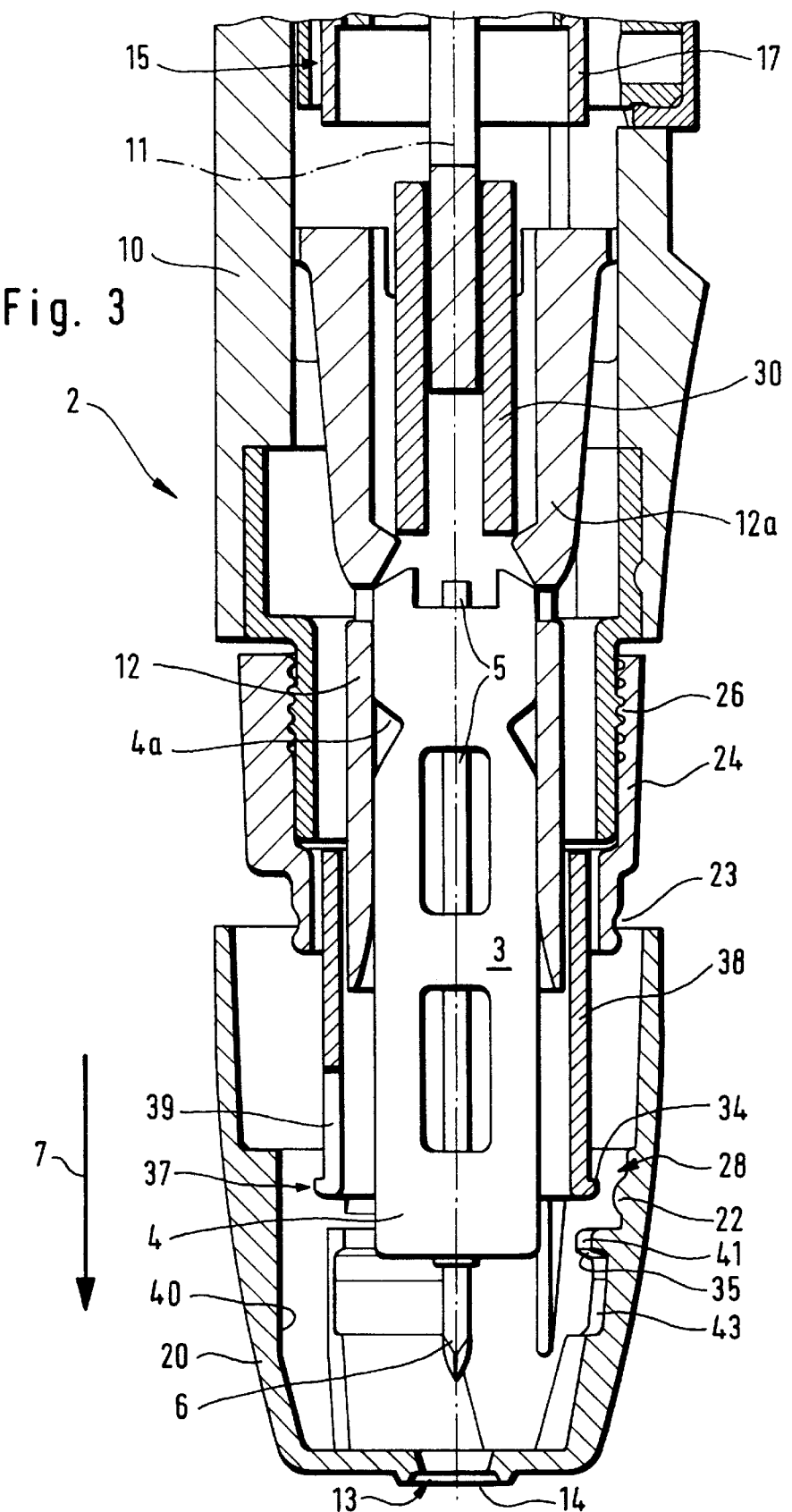

FIG. 1 shows a perspective exploded view of the front part of a blood lancet apparatus according to the invention, FIG. 2 shows a longitudinal section through the blood lancet apparatus in the state of utilization (lancet inserted, ejector retracted), FIG. 3 shows a longitudinal section according to FIG. 2 during the removal of the cap (lancet free, ejector pulled out)

Figure 6:
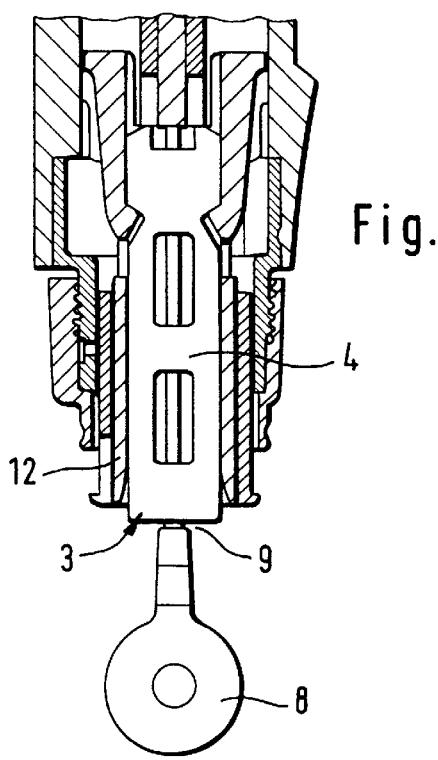
Figure 7:
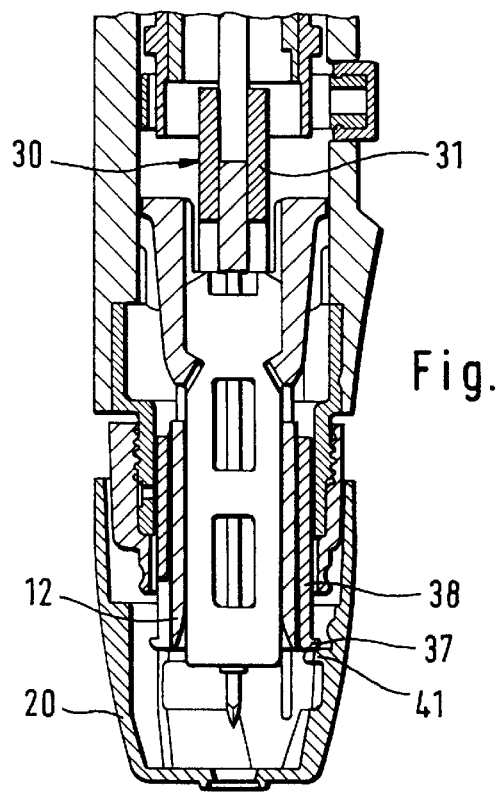
Figure 8:
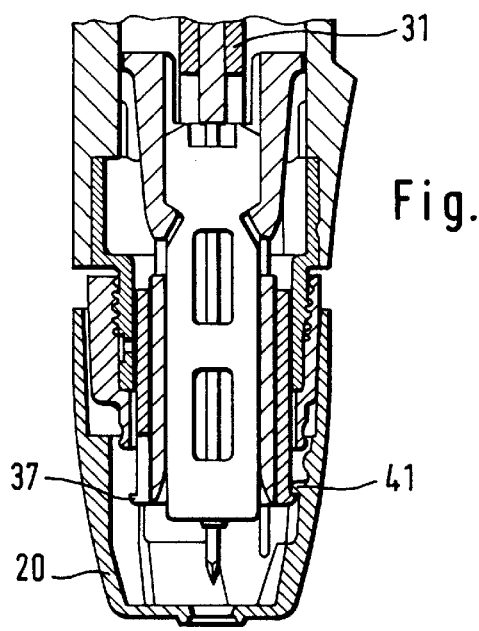
Figure 9:
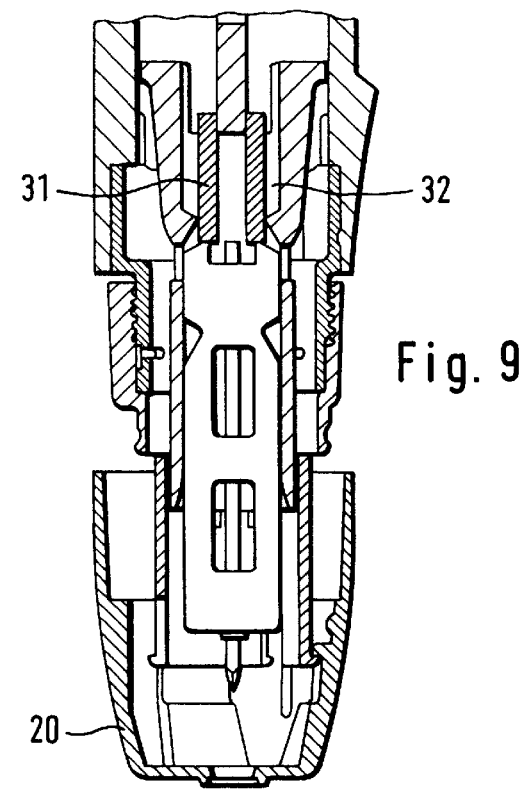

FIG. 4 shows a perspective view of the lancet holder, the lancet and the ejector in the position according to FIG. 2, FIG. 5 shows a perspective representation according to FIG. 4 without the lancet holder, FIG. 6 shows a longitudinal section according to FIG. 2 in reduced scale in a handling stage just after inserting a new lancet, FIG. 7 shows a longitudinal section according to FIG. 6 in a handling stage in which the housing cap is attached, FIG. 8 shows a longitudinal section according to FIG. 6 in a handling stage in which the housing cap is removed, FIG. 9 shows a longitudinal section according to FIG. 8 in a slightly later handling stage during removing of the housing cap.

The blood lancet system 1 represented in FIGS. 1 to 5 consists of a pricking apparatus 2 and exchangeable lancets 3, adapted to be used together with the pricking apparatus 2. The lancets 3 have a lancet body 4 made of plastic and a needle 5 fixed in the lancet body 4; the sharp tip 6 of the lancet needle 5 protrudes from the lancet body in the pricking direction symbolized by the arrow 7. For the unused lancet 3 represented in FIG. 1, the tip 6 is covered by a tip cover element 8, which is connected to the lancet body 4 via a breaking point 9 in a way that it can easily be removed by turning and pulling, thus exposing the tip 6.

In the embodiment shown, the housing 10 of the pricking apparatus 2 is designed with an elongated shape, similar to a pencil (so-called pencil-design). The longitudinal axis 11 of the pricking apparatus 2 runs in the pricking direction 7.

A lancet holder 12 is located in the housing 10. The lancet 3 is fixed in the lancet holder 12 by means of an appropriate clamping device in an exactly reproducible longitudinal position. In the represented case, the lancet holder 12 has two holder tongues 12a, precooked radially towards the interior of the holder and engaging with corresponding recesses 4a of the lancet body 4. Further characteristics of this fixing design can be taken from U.S. Pat. No. 5,318,584. The lancet holder is guided and arranged in a way that it can be moved forward, with as few vibrations as possible, in pricking direction 7 inside the housing 10, until the lancet tip 6 protrudes from an opening 13, thereby generating a prick wound in a body part 25 (FIG. 2) touching a contact surface 14 which is ring-shaped and surrounds the opening 13.

The pricking movement of the lancet holder 12 and a lancet 3 held thereby is driven by a lancet drive, designated as a whole as 15. The lancet drive is preferably designed according to the principles described in U.S. Pat. No. 5,318,584. This includes use of a cam control. A control pivot 16 (FIG. 4) is arranged at the lancet holder; it meshes, acting as operating cam, into a recess of a drive rotor 17 (only partially visible in FIGS. 2 and 3). The drive rotor 12 performs a turn around the longitudinal axis 11 of the housing 10. The rotation of the drive rotor 17 with the operating cam located therein, leads to a corresponding longitudinal movement of the control pivot 16, and thus of the lancet holder 12 in pricking direction 7. Further characteristics of this preferred lancet drive 15 can be taken from the US patent mentioned before.

The front end, in pricking direction, of the housing 10 is formed by a cap 20, covering the insertion end designed for inserting the lancet 3 into the lancet holder 12. The cap 20 is removeably fixed at the housing 10. To this end different fastening principles can be used, as long as a precise and reproducible definition of the longitudinal position of the housing cap 20 with respect to the lancet holder 12 is provided. For the design shown, a latch fastening is used, in which a bulge 22 provided at the cap 20 latches into a corresponding recess 23 of a housing part 24. Instead of such a latch fastening, a thread fastening can also be used.

In the embodiment shown, the housing part 24 to which the cap 20 is fastened, is adjustable in its longitudinal position in relation to the rest of the housing 10 and thus in relation to the lancet holder 12 by means of a thread 26. This allows an adjustment of the pricking depth. The more the housing part 24, and thus the cap 20 where the contact surface 14 is located, are shifted forwardly, in pricking direction 7, the smaller becomes the pricking depth, for a given lowest position of the lancet holder 12 in pricking direction 7.

A coupling mechanism 28, by which the lancet 3 and the housing cap 20 are coupled automatically to each other while the housing cap is attached the housing 10, includes an ejector 30 moveably arranged in pricking direction 7. It can best be seen in its entirety in FIG. 5. Generally, the ejector 30 may be formed by any constructive part comprising in its forwardly located section, with respect to the pricking direction, a coupling element 34 for coupling to the housing cap 20, and in its rearwardly located section a lancet contact element 31 which may contact the lancet 3 in such a way that movement of the lancet contact element 31 in pricking direction 7 causes ejection of the lancet 3 from the lancet holder 12. The part of the ejector 30 between the lancet contact element 31 and the coupling element 34 is designated intermediate part 33.

In the embodiment shown, the lancet contact element 31 is formed by two ejector rods 32, pushing against the rear end of the lancet 3. A coupling element 34 of the ejector 30 and a corresponding coupling element 35 of the housing cap 2 are adapted to each other such that the cap 20 is coupled to the ejector 30, and thus indirectly to the lancet 3, during attachment of the housing cap 20 to the housing 10. In the represented case, the ejector-side coupling element 34 is embodied by three segments of a radial collar 37, protruding radially outwardly from a sleeve 38 surrounding the lancet holder. The sleeve 38 has recesses in the area of the collar 37, separating the segments of the radial collar 37 from each other and allowing an elastic deformation, radially to the inside, of the sleeve 38 in the area of the radial collar 37.

In the embodiments shown, the coupling element 35 provided at the housing cap 20 is formed by a ring-shaped protrusion 41 located at the inside wall 40 of the housing, arranged and adapted in such a manner that during the attachment of the cap 20, the sleeve 38 is slightly compressed in the area of the radial collar 37, and the radial collar 37 latches, after passing the narrow formed by the ring-shaped protrusion 41, into a recess 43, which is located before the ring-shaped protrusion 41 in pricking direction 7.

Numerous variations of the coupling mechanism 28 are possible, provided that, on one hand, the coupling between the housing cap 20 and the lancet 3 (preferably indirectly via an ejector 30) is effected during attaching of the housing cap 20 onto the housing 10 (after previously having inserted the lancet 3 as a separate part into the lancet holder 12), and, on the other hand, the lancet 3 is during the removal of the cap 20 simultaneously pulled out of the lancet holder 12. The represented coupling principle, in which at least one of the coupling elements 34,35 is biased elastically in such a manner that it latches into a corresponding recess (here, the recess 43) of the other coupling element 35, is preferred, because it allows a particularly simple handling. However, an appropriate coupling can also be obtained, e.g., by a bayonet joint.

Furthermore, the contact between a lancet contact element 31 provided at the ejector 30 and the lancet, which is necessary for the removal of the lancet 3 from the lancet holder 12, must not necessarily be embodied by a push-out device, which pushes against the lancet from its rear end, as the ejector rod 32 does. A design which pulls the lancet 3 out of the lancet holder 12, is also possible in which case a lancet contact element provided at a correspondingly shaped ejector may latch into a corresponding recess of the lancet body, conveniently from the side.

The embodiment shown, in which the intermediate part 33 of the ejector 30 which joins the ejector-side coupling element 34 with the lancet contact element 31, is at least partially sleeve-shaped, is particularly preferred, as the sleeve 38 allows a precise guiding of the lancet holder 12 contained therein. Other designs are also possible. For example, the ejector can be formed by two or more rods arranged preferably rotation-symmetrically in pricking direction. At the front section of these rods, coupling elements for coupling to the cap 20 may be provided, and at their rear section, a lancet contact element 31 may be present.

FIGS. 6 to 9 show, complementary to the FIGS. 2 and 3, some more handling stages of the blood lancet system 1 according to the invention.

The lancet is gripped at the tip cover element 9 and inserted into the holder 12 (FIG. 6) with the housing cap 20 removed. Thereafter, the tip cover element 9 is turned off and the housing cap 20 is attached, its protrusion 41 pressing against the radial collar 37 of the sleeve 38, thus pushing the ejector 30 backwards, until its axial backward movement is stopped by a thrust block (FIG. 7).

If the housing cap (20) is further pushed backwards (into the position represented in FIG. 2), the ring-shaped protrusion 41 comes into an axial position behind the radial collar 37, so that the coupling elements 34,35 latch into each other.

After the pricking process, which is not different from previously known blood lancet systems, the housing cap 20 is removed again. During removal it reaches the position represented in FIG. 8, where the ring-shaped protrusion 41 is in contact with the radial collar 37. Thus, if the housing cap 20 is moved further in forward direction (in pricking direction 7), the ejector 30 is moved forward, pushing by means of its lancet contact element 31 (ejector rod 32) the lancet 3 out of the holder in forward direction. The lancet then falls into the housing cap 20 or remains unattached in the lower section of the housing 10. After taking off the housing cap 20, the used lancet 3 can be disposed into a waste bin without having to touch it.

What is claimed is:

1. Blood lancet system for blood withdrawal for diagnostic purposes, comprising
   a lancet and
   a pricking apparatus with a housing, a lancet holder movable in the housing for holding an exchangeable lancet, and a lancet drive for driving a pricking movement of the lancet on a predetermined pricking path,
   the housing comprises a cap to be attached at a forward end thereof in pricking direction, the cap being removable for removing a used lancet out of the housing,
   the lancet and the cap are adapted to be automatically coupled, during attaching the cap to the housing, by a coupling mechanism comprising matching coupling elements, thereby enabling the extraction of the lancet from the lancet holder without additional handling steps by removing the cap
   wherein
      the coupling mechanism comprises a movable ejector for ejecting the lancet, and
      a coupling element of the ejector and a corresponding coupling element of the cap are adapted to each other such that the cap is coupled to the ejector during attachment of the cap to the housing and during removal of the cap.

2. Blood lancet system according to claim 1, wherein at least one of the coupling elements has a protrusion, which is elastically biased in a direction transversal to the pricking direction and which latches during the coupling of the lancet and the cap into a corresponding recess of the other coupling element.

3. Blood lancet system according to claim 1, wherein the lancet comprises a lancet body made of plastic, a lancet needle fixed in the lancet body, and a tip cover element covering the lancet tip, the tip cover element being connected to the lancet body via a breaking point such that it can be removed after the insertion of the lancet into the lancet holder in order to expose the lancet tip protruding from the lancet body.

4. Blood lancet system according to claim 1, wherein
   the cap has a contact surface for contacting the blood lancet apparatus to the skin,
   the cap can be fixed to the housing at a defined position in the pricking direction, and
   the longitudinal position of the cap in the pricking direction can be adjusted by an adjustment device in order to adjust the pricking depth.

5. Blood lancet system according to claim 1, wherein the cap has a contact surface for contacting the blood lancet apparatus to the skin, the cap can be fixed to the housing at a defined position in the pricking direction, and the longitudinal position of the cap in the pricking direction can be adjusted by an adjustment device in order to adjust the pricking depth.

6. Blood lancet system for blood withdrawal for diagnostic purposes, comprising a lancet.

a pricking apparatus with a housing, a lancet holder movable in the housing for holding an exchangeable lancet, and a lancet drive for driving a pricking movement of the lancet on a predetermined pricking path, wherein the housing comprises a cap to be attached at a forward end thereof in pricking direction, the cap being removable for removing a used lancet out of the housing, and the lancet and the cap are adapted to be coupled, during attaching the cap to the housing, by a coupling mechanism comprising matching zoupling elements, thereby enabling the extraction of the lancet from the lancet holder by removing the cap, and an ejector which is movable in the housing in the pricking direction for ejecting the lancet from the lancet holder, is a component of the coupling mechanism, and has at a first end thereof a first of the matching coupling elements and at a second end thereof a lancet contact element contacting the lancet during the ejection thereof.

7. Blood lancet system according to claim 6, wherein a second of the matching coupling elements is arranged at the cap.

8. Blood lancet system according to claim 6, wherein the ejector has an intermediate part guided by a guide element such that it is movable parallel to the pricking path, the front end of the intermediate part being connected to the coupling element and the rear end of the intermediate part being connected to the lancet contact element.

9. Blood lancet system according to claim 8, wherein the movable intermediate part comprises a sleeve surrounding a lancet which is inserted in the holder.

10. Blood lancet system according to claim 6, wherein the cap has a contact surface for contacting the blood lancet apparatus to the skin, the cap can be fixed to the housing at a defined position in the pricking direction, and the longitudinal position of the cap in the pricking direction can be adjusted by an adjustment device in order to adjust the pricking depth.

11. Blood lancet system according to claim 6, wherein at least one of the coupling elements has a protrusion which is elastically biased in a direction transversal to the pricking direction and which latches during the coupling of the lancet and the cap into a corresponding recess of the other coupling element.

12. Blood lancet system according to claim 6, wherein the lancet comprises a lancet body made of plastic, a lancet needle fixed in the lancet body, and a tip cover element covering the lancet tip, the tip cover element being connected to the lancet body via a breaking point such that it can be removed after the insertion of the lancet into the lancet holder in order to expose the lancet tip protruding from the lancet body.

13. Blood lancet system according to claim 6, wherein the cap has a contact surface for contacting the blood lancet apparatus to the skin, the cap can be fixed to the housing at a defined position in the pricking direction, and the longitudinal position of the cap in the pricking direction can be adjusted by an adjustment device in order to adjust the pricking depth.

14. Blood lancet system for blood withdrawal for diagnostic purposes, comprising a lancet and a pricking apparatus with a housing, a lancet holder movable in the housing for holding an exchangeable lancet, and a lancet drive for driving a pricking movement of the lancet on a predetermined pricking path, the housing comprising a cap to be attached at a forward end thereof in pricking direction, the cap being removable for removing a used lancet out of the housing, the lancet and the cap being adapted to be automatically coupled, during attaching the cap to the housing, by a coupling mechanism comprising matching coupling elements, thereby enabling the extraction of the lancet from the lancet holder without additional handling steps by removing the cap, wherein the coupling mechanism comprises a movable ejector for ejecting the lancet, a coupling element of the ejector and a corresponding coupling element of the cap are adapted to each other such that the cap is coupled to the ejector during attachment of the cap to the housing and during removal of the cap after the pricking action the lancet is ejected from the lancet holder in such a manner that the used lancet falls into the cap or remains unattached in the lower section of the housing, whereby the used lancet can be disposed without user contact.

15. Blood lancet system according to claim 14, wherein a second of the matching coupling elements is arranged at the cap.

16. Blood lancet system according to claim 14, wherein the ejector has an intermediate part guided by a guide element such that it is movable parallel to the pricking path, the front end of the intermediate part being connected to the coupling element and the rear end of the intermediate part being connected to the lancet contact element.

17. Blood lancet system according to claim 16, wherein the movable intermediate part comprises a sleeve surrounding a lancet which is inserted in the holder.

18. Blood lancet system according to claim 14, wherein at least one of the coupling elements has a protrusion which is elastically biased in a direction transversal to the pricking direction and which latches during the coupling of the lancet and the cap into a corresponding recess of the other coupling element.

19. Blood lancet system according to claim 14, wherein the lancet comprises a lancet body made of plastic, a lancet needle fixed in the lancet body, and a tip cover element covering the lancet tip, the tip cover element being connected to the lancet body via a breaking point such that it can be removed after the insertion of the lancet into the lancet holder in order to expose the lancet tip protruding from the lancet body.

20. Blood lancet system according to claim 14, wherein the cap has a contact surface for contacting the blood lancet apparatus to the skin, the cap can be fixed to the housing at a defined position in the pricking direction, and the longitudinal position of the cap in the pricking direction can be adjusted by an adjustment device in order to adjust the pricking depth.

* * * * *